(12) United States Patent
Bagnoli et al.

(10) Patent No.: US 9,926,344 B2
(45) Date of Patent: Mar. 27, 2018

(54) **STABILISED PROTEINS FOR IMMUNISING AGAINST *STAPHYLOCOCCUS AUREUS***

(71) Applicant: GlaxoSmithKline Biologicals SA, Rixensart (BE)

(72) Inventors: Fabio Bagnoli, Monteriggioni (IT); Fabiana Falugi, Chicago, IL (US); Guido Grandi, Segrate (IT); Massimo Mariani, Siena (IT); Mikkel Nissum, Casciano di Murlo (IT); Michele Pallaoro, Siena (IT); Silvana Savino, Tavarnelle Val di Pesa (IT)

(73) Assignee: GLAXOSMITHKLINE BIOLOGICALS SA (BE)

( * ) Notice: Subject to any disclaimer, the term of this patent is extended or adjusted under 35 U.S.C. 154(b) by 106 days.

(21) Appl. No.: 14/420,831

(22) PCT Filed: Aug. 29, 2013

(86) PCT No.: PCT/EP2013/067853
§ 371 (c)(1),
(2) Date: Feb. 10, 2015

(87) PCT Pub. No.: WO2014/033190
PCT Pub. Date: Mar. 6, 2014

(65) Prior Publication Data
US 2015/0203542 A1    Jul. 23, 2015

Related U.S. Application Data

(60) Provisional application No. 61/695,723, filed on Aug. 31, 2012.

(51) Int. Cl.
*C07K 14/31* (2006.01)
*A61K 39/085* (2006.01)
*A61K 39/00* (2006.01)

(52) U.S. Cl.
CPC ............ *C07K 14/31* (2013.01); *A61K 39/085* (2013.01); *A61K 2039/55505* (2013.01)

(58) Field of Classification Search
None
See application file for complete search history.

(56) References Cited

U.S. PATENT DOCUMENTS

| | | | |
|---|---|---|---|
| 5,874,238 A | 2/1999 | Potempa et al. | |
| 6,080,725 A | 6/2000 | Marciani | |
| 6,355,271 B1 | 3/2002 | Bell et al. | |
| 6,630,161 B1 | 10/2003 | Leesman | |
| 7,608,276 B2 * | 10/2009 | Masignani | C07K 14/31 424/184.1 |
| 2007/0014805 A1 | 1/2007 | Dalencon et al. | |
| 2007/0191314 A1 | 8/2007 | Klucker et al. | |
| 2015/0044251 A1 | 2/2015 | Contorni et al. | |
| 2016/0051667 A1 * | 2/2016 | Berti | A61K 47/48261 424/194.1 |

FOREIGN PATENT DOCUMENTS

| | | | |
|---|---|---|---|
| EP | 0355460 A2 | 2/1990 | |
| JP | S624300 A | 1/1987 | |
| WO | WO-9014837 A1 | 12/1990 | |
| WO | WO-9511700 A1 | 5/1995 | |
| WO | WO-0023105 A2 | 4/2000 | |
| WO | WO-0160851 A1 | 8/2001 | |
| WO | WO-0187925 A2 | 11/2001 | |
| WO | WO-0294868 A2 | 11/2002 | |
| WO | WO-2005097181 A1 | 10/2005 | |
| WO | WO-2006110603 A1 | 10/2006 | |
| WO | WO-2006113373 A2 | 10/2006 | |
| WO | WO-2007044382 A2 | 4/2007 | |
| WO | WO-2008019162 A2 | 2/2008 | |
| WO | WO-2008043774 A1 | 4/2008 | |
| WO | WO-2010119343 A2 | 10/2010 | |
| WO | WO-2011027222 A2 | 3/2011 | |
| WO | WO-2011051917 A1 | 5/2011 | |
| WO | WO 2011138636 A1 * | 11/2011 | ....... A61K 47/48261 |
| WO | WO 2013030378 A1 * | 3/2013 | .......... A61K 39/085 |

OTHER PUBLICATIONS

Chen et al. 2013 (Complete Genome Sequence of *Staphylococcus aureus* z172, a Vancomycin-Intermediate and Daptomycin-Nonsusceptible Methicillin-Resistant Strain Isolated in Taiwan; Genome Announcements; 1(6):1-2).*
Greenspan et al. 1999 (Defining epitopes: It's not as easy as it seems; Nature Biotechnology, 17:936-937).*
Shinefield et al. 2002 (Use of a *Staphylococcus aureus* conjugate vaccine in patients receiving hemodialysis; New England Journal of Medicine, vol. 346, No. 7: 491-496).*
Harro et al. (2010) "Safety and immunogenicity of a novel *Staphylococcus aureus* vaccine: results from the first study of the vaccine dose range in humans." Clin Vaccine Immunol 17:1868-74.
Kuklin et al. (2006) "A novel *Staphylococcus aureus* vaccine: iron surface determinant B induces rapid antibody responses in rhesus macaques and specific increased survival in a murine *S. aureus* sepsis model." Infect Immun. 74(4):2215-23.
Kuroda et al. (2001) "Whole genome sequencing of meticillin-resistant *Staphylococcus aureus*." Lancet 357:1225-1240.
Sebulsky & Heinrichs (2001) "Identification and characterization of fhuD1 and fhuD2, two genes involved in iron-hydroxamate uptake in *Staphylococcus aureus*." J Bacteriol 183:4994-5000.
Sebulsky et al. (2003) "The role of FhuD2 in iron(III)-hydroxamate transport in *Staphylococcus aureus*. Demonstration that FhuD2 binds iron(III)-hydroxamates but with minimal conformational change and implication of mutations on transport." J Biol Chem 278:49890-900.
Stranger-Jones et al. (2006) "Vaccine assembly from surface proteins of *Staphylococcus aureus*." PNAS USA 103:16942-7.
Wardenburg et al. (2007) "Surface proteins and exotoxins are required for the pathogenesis of *Staphylococcus aureus* pneumonia." Infect Immun 75:1040-4.

* cited by examiner

*Primary Examiner* — Mary Lyons
(74) *Attorney, Agent, or Firm* — Joseph Schuller

(57) ABSTRACT

Elimination of disulphide bond formation of cysteine-containing *S. aureus* antigens enhances antigen stability. The invention provides variant forms of cysteine-containing *S. aureus* antigen with a point mutation that replaces, deletes or modifies the cysteine residue.

11 Claims, 3 Drawing Sheets

SEQUENCE LISTING

<160> NUMBER OF SEQ IDS NOS: 7

<210> SEQ ID NO 1
<211> LENGTH: 302
<212> TYPE: PRT
<213> ORGANISM: staphylococcus aureus

<400> SEQUENCE: 1

```
Met Lys Lys Leu Leu Leu Pro Leu Ile Ile Met Leu Leu Val Leu Ala
1               5                   10                  15

Ala Cys Gly Asn Gln Gly Glu Lys Asn Asn Lys Ala Glu Thr Lys Ser
            20                  25                  30

Tyr Lys Met Asp Asp Gly Lys Thr Val Asp Ile Pro Lys Asp Pro Lys
        35                  40                  45

Arg Ile Ala Val Val Ala Pro Thr Tyr Ala Gly Gly Leu Lys Lys Leu
    50                  55                  60

Gly Ala Asn Ile Val Ala Val Asn Gln Gln Val Asp Gln Ser Lys Val
65                  70                  75                  80

Leu Lys Asp Lys Phe Lys Gly Val Thr Lys Ile Gly Asp Gly Asp Val
                85                  90                  95

Glu Lys Val Ala Lys Glu Lys Pro Asp Leu Ile Ile Val Tyr Ser Thr
            100                 105                 110

Asp Lys Asp Ile Lys Lys Tyr Gln Lys Val Ala Pro Thr Val Val Val
        115                 120                 125

Asp Tyr Asn Lys His Lys Tyr Leu Glu Gln Gln Glu Met Leu Gly Lys
    130                 135                 140

Ile Val Gly Lys Glu Asp Lys Val Lys Ala Trp Lys Lys Asp Trp Glu
145                 150                 155                 160

Glu Thr Thr Ala Lys Asp Gly Lys Glu Ile Lys Lys Ala Ile Gly Gln
            165                 170                 175

Asp Ala Thr Val Ser Leu Phe Asp Glu Phe Asp Lys Lys Leu Tyr Thr
        180                 185                 190

Tyr Gly Asp Asn Trp Gly Arg Gly Gly Glu Val Leu Tyr Gln Ala Phe
    195                 200                 205

Gly Leu Lys Met Gln Pro Glu Gln Gln Lys Leu Thr Ala Lys Ala Gly
210                 215                 220

Trp Ala Glu Val Lys Gln Glu Glu Ile Glu Lys Tyr Ala Gly Asp Tyr
225                 230                 235                 240

Ile Val Ser Thr Ser Glu Gly Lys Pro Thr Pro Gly Tyr Glu Ser Thr
            245                 250                 255

Asn Met Trp Lys Asn Leu Lys Ala Thr Lys Glu Gly His Ile Val Lys
        260                 265                 270

Val Asp Ala Gly Thr Tyr Trp Tyr Asn Asp Pro Tyr Thr Leu Asp Phe
    275                 280                 285

Met Arg Lys Asp Leu Lys Glu Leu Leu Ile Lys Ala Ala Lys
290                 295                 300
```

<210> SEQ ID NO 2
<211> LENGTH: 285
<212> TYPE: PRT
<213> ORGANISM: staphylococcus aureus

<400> SEQUENCE: 2

```
Cys Gly Asn Gln Gly Glu Lys Asn Asn Lys Ala Glu Thr Lys Ser Tyr
1               5                   10                  15

Lys Met Asp Asp Gly Lys Thr Val Asp Ile Pro Lys Asp Pro Lys Arg
```

```
            20                  25                  30
Ile Ala Val Val Ala Pro Thr Tyr Ala Gly Gly Leu Lys Lys Leu Gly
             35                  40                  45

Ala Asn Ile Val Ala Val Asn Gln Gln Val Asp Gln Ser Lys Val Leu
 50                  55                  60

Lys Asp Lys Phe Lys Gly Val Thr Lys Ile Gly Asp Gly Asp Val Glu
 65                  70                  75                  80

Lys Val Ala Lys Glu Lys Pro Asp Leu Ile Ile Val Tyr Ser Thr Asp
                 85                  90                  95

Lys Asp Ile Lys Lys Tyr Gln Lys Val Ala Pro Thr Val Val Asp
            100                 105                 110

Tyr Asn Lys His Lys Tyr Leu Glu Gln Gln Glu Met Leu Gly Lys Ile
            115                 120                 125

Val Gly Lys Glu Asp Lys Val Lys Ala Trp Lys Asp Trp Glu Glu
            130                 135                 140

Thr Thr Ala Lys Asp Gly Lys Glu Ile Lys Lys Ala Ile Gly Gln Asp
145                 150                 155                 160

Ala Thr Val Ser Leu Phe Asp Glu Phe Asp Lys Lys Leu Tyr Thr Tyr
                165                 170                 175

Gly Asp Asn Trp Gly Arg Gly Gly Glu Val Leu Tyr Gln Ala Phe Gly
                180                 185                 190

Leu Lys Met Gln Pro Glu Gln Gln Lys Leu Thr Ala Lys Ala Gly Trp
            195                 200                 205

Ala Glu Val Lys Gln Glu Glu Ile Gly Lys Tyr Ala Gly Asp Tyr Ile
            210                 215                 220

Val Ser Thr Ser Glu Gly Lys Pro Thr Pro Gly Tyr Glu Ser Thr Asn
225                 230                 235                 240

Met Trp Lys Asn Leu Lys Ala Thr Lys Glu Gly His Ile Val Lys Val
                245                 250                 255

Asp Ala Gly Thr Tyr Trp Tyr Asn Asp Pro Tyr Thr Leu Asp Phe Met
                260                 265                 270

Arg Lys Asp Leu Lys Glu Lys Leu Ile Lys Ala Ala Lys
            275                 280                 285

<210> SEQ ID NO 3
<211> LENGTH: 288
<212> TYPE: PRT
<213> ORGANISM: Artificial Sequence
<220> FEATURE:
<223> OTHER INFORMATION: staphylococcus aureus protein variant

<400> SEQUENCE: 3

Met Ala Ser Cys Gly Asn Gln Gly Glu Lys Asn Asn Lys Ala Glu Thr
1                5                  10                  15

Lys Ser Tyr Lys Met Asp Asp Gly Lys Thr Val Asp Ile Pro Lys Asp
             20                  25                  30

Pro Lys Arg Ile Ala Val Val Ala Pro Thr Tyr Ala Gly Gly Leu Lys
             35                  40                  45

Lys Leu Gly Ala Asn Ile Val Ala Val Asn Gln Gln Val Asp Gln Ser
 50                  55                  60

Lys Val Leu Lys Asp Lys Phe Lys Gly Val Thr Lys Ile Gly Asp Gly
 65                  70                  75                  80

Asp Val Glu Lys Val Ala Lys Glu Lys Pro Asp Leu Ile Ile Val Tyr
                 85                  90                  95

Ser Thr Asp Lys Asp Ile Lys Lys Tyr Gln Lys Val Ala Pro Thr Val
```

```
            100                 105                 110
Val Val Asp Tyr Asn Lys His Lys Tyr Leu Glu Gln Gln Glu Met Leu
                115                 120                 125
Gly Lys Ile Val Gly Lys Glu Asp Lys Val Lys Ala Trp Lys Lys Asp
            130                 135                 140
Trp Glu Glu Thr Thr Ala Lys Asp Gly Lys Glu Ile Lys Lys Ala Ile
145                 150                 155                 160
Gly Gln Asp Ala Thr Val Ser Leu Phe Asp Glu Phe Asp Lys Lys Leu
                165                 170                 175
Tyr Thr Tyr Gly Asp Asn Trp Gly Arg Gly Gly Glu Val Leu Tyr Gln
                180                 185                 190
Ala Phe Gly Leu Lys Met Gln Pro Glu Gln Gln Lys Leu Thr Ala Lys
            195                 200                 205
Ala Gly Trp Ala Glu Val Lys Gln Glu Glu Ile Glu Lys Tyr Ala Gly
            210                 215                 220
Asp Tyr Ile Val Ser Thr Ser Glu Gly Lys Pro Thr Pro Gly Tyr Glu
225                 230                 235                 240
Ser Thr Asn Met Trp Lys Asn Leu Lys Ala Thr Lys Glu Gly His Ile
                245                 250                 255
Val Lys Val Asp Ala Gly Thr Tyr Trp Tyr Asn Asp Pro Tyr Thr Leu
                260                 265                 270
Asp Phe Met Arg Lys Asp Leu Lys Glu Lys Leu Ile Lys Ala Ala Lys
                275                 280                 285

<210> SEQ ID NO 4
<211> LENGTH: 284
<212> TYPE: PRT
<213> ORGANISM: Artificial Sequence
<220> FEATURE:
<223> OTHER INFORMATION: staphylococcus aureus protein variant

<400> SEQUENCE: 4

Gly Asn Gln Gly Glu Lys Asn Asn Lys Ala Thr Lys Ser Tyr Lys
1               5                   10                  15
Met Asp Asp Gly Lys Thr Val Asp Ile Pro Lys Asp Pro Lys Arg Ile
                20                  25                  30
Ala Val Val Ala Pro Thr Tyr Ala Gly Gly Leu Lys Lys Leu Gly Ala
            35                  40                  45
Asn Ile Val Ala Val Asn Gln Gln Val Asp Gln Ser Lys Val Leu Lys
        50                  55                  60
Asp Lys Phe Lys Gly Val Thr Lys Ile Gly Asp Gly Asp Val Glu Lys
65                  70                  75                  80
Val Ala Lys Glu Lys Pro Asp Leu Ile Ile Val Tyr Ser Thr Asp Lys
                85                  90                  95
Asp Ile Lys Lys Tyr Gln Lys Val Ala Pro Thr Val Val Asp Tyr
                100                 105                 110
Asn Lys His Lys Tyr Leu Glu Gln Gln Glu Met Leu Gly Lys Ile Val
            115                 120                 125
Gly Lys Glu Asp Lys Val Lys Ala Trp Lys Lys Asp Trp Glu Glu Thr
        130                 135                 140
Thr Ala Lys Asp Gly Lys Glu Ile Lys Lys Ala Ile Gly Gln Asp Ala
145                 150                 155                 160
Thr Val Ser Leu Phe Asp Glu Phe Asp Lys Lys Leu Tyr Thr Tyr Gly
                165                 170                 175
Asp Asn Trp Gly Arg Gly Gly Glu Val Leu Tyr Gln Ala Phe Gly Leu
```

```
                    180                 185                 190
Lys Met Gln Pro Glu Gln Gln Lys Leu Thr Ala Lys Ala Gly Trp Ala
            195                 200                 205

Glu Val Lys Gln Glu Glu Ile Glu Lys Tyr Ala Gly Asp Tyr Ile Val
        210                 215                 220

Ser Thr Ser Glu Gly Lys Pro Thr Pro Gly Tyr Glu Ser Thr Asn Met
225                 230                 235                 240

Trp Lys Asn Leu Lys Ala Thr Lys Glu Gly His Ile Val Lys Val Asp
            245                 250                 255

Ala Gly Thr Tyr Trp Tyr Asn Asp Pro Tyr Thr Leu Asp Phe Met Arg
        260                 265                 270

Lys Asp Leu Lys Glu Lys Leu Ile Lys Ala Ala Lys
            275                 280

<210> SEQ ID NO 5
<211> LENGTH: 285
<212> TYPE: PRT
<213> ORGANISM: Artificial Sequence
<220> FEATURE:
<223> OTHER INFORMATION: staphylococcus aureus protein variant
<220> FEATURE:
<221> NAME/KEY: Xaa
<222> LOCATION: 1
<223> OTHER INFORMATION: Any amino acid that does not contain a free
      thiol group.

<400> SEQUENCE: 5

Xaa Gly Asn Gln Gly Glu Lys Asn Asn Lys Ala Glu Thr Lys Ser Tyr
1               5                   10                  15

Lys Met Asp Asp Gly Lys Thr Val Asp Ile Pro Lys Asp Pro Lys Arg
            20                  25                  30

Ile Ala Val Val Ala Pro Thr Tyr Ala Gly Gly Leu Lys Lys Leu Gly
        35                  40                  45

Ala Asn Ile Val Ala Val Asn Gln Gln Val Asp Gln Ser Lys Val Leu
    50                  55                  60

Lys Asp Lys Phe Lys Gly Val Thr Lys Ile Gly Asp Gly Asp Val Glu
65                  70                  75                  80

Lys Val Ala Lys Glu Lys Pro Asp Leu Ile Ile Val Tyr Ser Thr Asp
                85                  90                  95

Lys Asp Ile Lys Lys Tyr Gln Lys Val Ala Pro Thr Val Val Val Asp
            100                 105                 110

Tyr Asn Lys His Lys Tyr Leu Glu Gln Gln Glu Met Leu Gly Lys Ile
        115                 120                 125

Val Gly Lys Glu Asp Lys Val Lys Ala Trp Lys Lys Asp Trp Glu Glu
    130                 135                 140

Thr Thr Ala Lys Asp Gly Lys Glu Ile Lys Lys Ala Ile Gly Gln Asp
145                 150                 155                 160

Ala Thr Val Ser Leu Phe Asp Glu Phe Asp Lys Lys Leu Tyr Thr Tyr
                165                 170                 175

Gly Asp Asn Trp Gly Arg Gly Gly Glu Val Leu Tyr Gln Ala Phe Gly
            180                 185                 190

Leu Lys Met Gln Pro Glu Gln Gln Lys Leu Thr Ala Lys Ala Gly Trp
        195                 200                 205

Ala Glu Val Lys Gln Glu Glu Ile Glu Lys Tyr Ala Gly Asp Tyr Ile
    210                 215                 220

Val Ser Thr Ser Glu Gly Lys Pro Thr Pro Gly Tyr Glu Ser Thr Asn
225                 230                 235                 240
```

Met Trp Lys Asn Leu Lys Ala Thr Lys Glu Gly His Ile Val Lys Val
            245                 250                 255

Asp Ala Gly Thr Tyr Trp Tyr Asn Asp Pro Tyr Thr Leu Asp Phe Met
            260                 265                 270

Arg Lys Asp Leu Lys Glu Lys Leu Ile Lys Ala Ala Lys
            275                 280                 285

<210> SEQ ID NO 6
<211> LENGTH: 287
<212> TYPE: PRT
<213> ORGANISM: Artificial Sequence
<220> FEATURE:
<223> OTHER INFORMATION: staphylococcus aureus protein variant

<400> SEQUENCE: 6

Met Ala Ser Gly Asn Gln Gly Glu Lys Asn Asn Lys Ala Glu Thr Lys
1               5                   10                  15

Ser Tyr Lys Met Asp Asp Gly Lys Thr Val Asp Ile Pro Lys Asp Pro
            20                  25                  30

Lys Arg Ile Ala Val Val Ala Pro Thr Tyr Ala Gly Gly Leu Lys Lys
        35                  40                  45

Leu Gly Ala Asn Ile Val Ala Val Asn Gln Gln Val Asp Gln Ser Lys
50                  55                  60

Val Leu Lys Asp Lys Phe Lys Gly Val Thr Lys Ile Gly Asp Gly Asp
65                  70                  75                  80

Val Glu Lys Val Ala Lys Glu Lys Pro Asp Leu Ile Ile Val Tyr Ser
                85                  90                  95

Thr Asp Lys Asp Ile Lys Lys Tyr Gln Lys Val Ala Pro Thr Val Val
            100                 105                 110

Val Asp Tyr Asn Lys His Lys Tyr Leu Glu Gln Gln Glu Met Leu Gly
        115                 120                 125

Lys Ile Val Gly Lys Glu Asp Lys Val Lys Ala Trp Lys Lys Asp Trp
130                 135                 140

Glu Glu Thr Thr Ala Lys Asp Gly Lys Glu Ile Lys Lys Ala Ile Gly
145                 150                 155                 160

Gln Asp Ala Thr Val Ser Leu Phe Asp Glu Phe Lys Lys Leu Tyr
                165                 170                 175

Thr Tyr Gly Asp Asn Trp Gly Arg Gly Gly Glu Val Leu Tyr Gln Ala
            180                 185                 190

Phe Gly Leu Lys Met Gln Pro Glu Gln Gln Lys Leu Thr Ala Lys Ala
        195                 200                 205

Gly Trp Ala Glu Val Lys Gln Glu Ile Glu Lys Tyr Ala Gly Asp
210                 215                 220

Tyr Ile Val Ser Thr Ser Glu Gly Lys Pro Thr Pro Gly Tyr Glu Ser
225                 230                 235                 240

Thr Asn Met Trp Lys Asn Leu Lys Ala Thr Lys Glu Gly His Ile Val
                245                 250                 255

Lys Val Asp Ala Gly Thr Tyr Trp Tyr Asn Asp Pro Tyr Thr Leu Asp
            260                 265                 270

Phe Met Arg Lys Asp Leu Lys Glu Lys Leu Ile Lys Ala Ala Lys
        275                 280                 285

<210> SEQ ID NO 7
<211> LENGTH: 288
<212> TYPE: PRT
<213> ORGANISM: Artificial Sequence

```
<220> FEATURE:
<223> OTHER INFORMATION: staphylococcus aureus protein variant
<220> FEATURE:
<221> NAME/KEY: Xaa
<222> LOCATION: 4
<223> OTHER INFORMATION: Any amino acid that does not contain a free
      thiol group.

<400> SEQUENCE: 7

Met Ala Ser Xaa Gly Asn Gln Gly Glu Lys Asn Asn Lys Ala Glu Thr
1               5                   10                  15

Lys Ser Tyr Lys Met Asp Asp Gly Lys Thr Val Asp Ile Pro Lys Asp
            20                  25                  30

Pro Lys Arg Ile Ala Val Val Ala Pro Thr Tyr Ala Gly Gly Leu Lys
        35                  40                  45

Lys Leu Gly Ala Asn Ile Val Ala Val Asn Gln Gln Val Asp Gln Ser
    50                  55                  60

Lys Val Leu Lys Asp Lys Phe Lys Gly Val Thr Lys Ile Gly Asp Gly
65                  70                  75                  80

Asp Val Glu Lys Val Ala Lys Glu Lys Pro Asp Leu Ile Ile Val Tyr
                85                  90                  95

Ser Thr Asp Lys Asp Ile Lys Lys Tyr Gln Lys Val Ala Pro Thr Val
                100                 105                 110

Val Val Asp Tyr Asn Lys His Lys Tyr Leu Glu Gln Gln Glu Met Leu
            115                 120                 125

Gly Lys Ile Val Gly Lys Glu Asp Lys Val Lys Ala Trp Lys Lys Asp
    130                 135                 140

Trp Glu Glu Thr Thr Ala Lys Asp Gly Lys Glu Ile Lys Lys Ala Ile
145                 150                 155                 160

Gly Gln Asp Ala Thr Val Ser Leu Phe Asp Glu Phe Asp Lys Lys Leu
                165                 170                 175

Tyr Thr Tyr Gly Asp Asn Trp Gly Arg Gly Gly Glu Val Leu Tyr Gln
                180                 185                 190

Ala Phe Gly Leu Lys Met Gln Pro Glu Gln Gln Lys Leu Thr Ala Lys
            195                 200                 205

Ala Gly Trp Ala Glu Val Lys Gln Glu Glu Ile Glu Lys Tyr Ala Gly
        210                 215                 220

Asp Tyr Ile Val Ser Thr Ser Glu Gly Lys Pro Thr Pro Gly Tyr Glu
225                 230                 235                 240

Ser Thr Asn Met Trp Lys Asn Leu Lys Ala Thr Lys Glu Gly His Ile
                245                 250                 255

Val Lys Val Asp Ala Gly Thr Tyr Trp Tyr Asn Asp Pro Tyr Thr Leu
                260                 265                 270

Asp Phe Met Arg Lys Asp Leu Lys Glu Lys Leu Ile Lys Ala Ala Lys
                275                 280                 285
```

STABILISED PROTEINS FOR IMMUNISING AGAINST *STAPHYLOCOCCUS AUREUS*

RELATED APPLICATIONS

This patent application is a 35 U.S.C. § 371 National Stage of International Application No. PCT/EP2013/067853, entitled "STABILISED PROTEINS FOR IMMUNISING AGAINST *STAPHYLOCOCCUS AUREUS*" filed Aug. 29, 2013, which claims the benefit of and priority to U.S. Provisional Application 61/695,723, filed Aug. 31, 2012, the contents of each of which are hereby incorporated by reference in their entirety.

SEQUENCE LISTING

The present application contains a Sequence Listing, which has been submitted in ASCII format via EFS-Web and is hereby incorporated by reference in its entirety. The ASCII copy, created on Aug. 28, 2013, is named PAT055151-WO-PCT_SequenceListing.TXT and is 18 kilobytes in size.

TECHNICAL FIELD

This invention relates to immunogenic compositions comprising antigens derived from *Staphylococcus aureus* and to their use in immunisation.

BACKGROUND ART

*S. aureus* is a Gram-positive spherical bacterium and is the leading cause of infection of the bloodstream, lower respiratory tract, and skin and other soft tissues. It causes a range of illnesses from minor skin infections to life-threatening diseases including pneumonia and septicaemia, and the mortality associated with *S. aureus* per annum in the US exceeds that of any other infectious disease, including HIV/AIDS.

There is currently no authorised vaccine against *S. aureus*. A vaccine based on a mixture of surface polysaccharides from bacterial types 5 and 8, StaphVAX™, failed to reduce infections when compared to the placebo group in a phase III clinical trial in 2005. Reference 1 reports data on the "V710" vaccine from Merck and Intercell which is based on a single antigen, IsdB, a conserved iron-sequestering cell-surface protein [2,3]. However, the clinical trials of V710 were terminated in 2011 based on the observation that V710 was unlikely to demonstrate a statistically significant clinical benefit, and a safety concern regarding overall mortality and multi-organ dysfunction that occurred with greater frequency in vaccine recipients compared with placebo recipients [4].

Reference 5 discloses various *S. aureus* antigens and their combinations as vaccine strategics. Reference 6 discloses that *S. aureus* polypeptide antigens can be unstable in a simple buffer solution, and that antigens can be stabilised by the presence of a stabilizing additive, e.g. EDTA. Instability of the antigens is undesirable because (1) it does not allow vaccines to be stored for a long period of time before administration, and (2) inconsistency of vaccines from batch to batch can affect quality and regulatory approval requirements. Furthermore, manufacture of vaccines containing these unstable antigens can be complicated and involve multiple purification steps. Therefore it is an object of the invention to identify further strategies to stabilize *S. aureus* polypeptide antigens in immunogenic compositions.

DISCLOSURE OF THE INVENTION

The inventors have found that preventing oligomerization of antigens is an effective strategy to enhance antigen stability. Various *S. aureus* antigens contain cysteine residues, and they can form oligomers in standard buffer solutions, including covalent dimers formed by disulphide bonds between cysteine residues. The inventors have found that compositions containing these covalent dimers can be unstable, and may form aggregates or influence the stability of the other antigens in the composition, if present. Covalent dimer formation can be prevented by replacing, modifying or deleting the cysteine residues such that disulphide bond formation is eliminated. Interestingly, preventing these antigens to form covalent dimers improves antigen stability and keeps a high total selectivity of the composition (i.e. a high proportion of single isoform relative to total antigen) and purity. Furthermore, the inventors found that these cysteine-deficient antigens remain effective in eliciting an immune response against the wild-type cysteine-containing antigens. Therefore, cysteine-deficient antigens can be included in vaccine formulations to improve antigen stability.

The Sta006 antigen naturally has a N-terminus cysteine in its mature form. The inventors found that deletion of cysteine stops dimerization and gives a protein which is easier to characterise and analyse, without negatively impacting immunogenicity. Compositions containing the cysteine-deficient Sta006 antigens are more stable. Thus, the invention provides a polypeptide comprising an amino acid sequence that has at least 90% (e.g. ≥91%, ≥92%, ≥93%, ≥94%, ≥95%, ≥96%, ≥97%, ≥98%, ≥99%, ≥99.5%) identity to SEQ ID NO: 4, wherein the polypeptide has no free thiol group, and can elicit antibodies (e.g. when administered to a human) which recognise a wild-type Sta006 antigen (e.g. a *S. aureus* protein consisting of amino acid sequence SEQ ID NO: 2). The polypeptide cannot form covalent dimers via disulphide bonds.

The invention provides an immunogenic composition comprising a polypeptide of the invention. The composition can be in aqueous form, in which case it ideally has a pH of between 5 and 8. The composition may also include an adjuvant e.g. an aluminium salt.

In some embodiments of the invention, the immunogenic composition comprises further antigens which can be polypeptides and/or saccharides. For example, they can also include one or more *S. aureus* capsular saccharide conjugate(s) e.g. against a serotype 5 and/or a serotype 8 strain. In other embodiments, the composition includes no additional staphylococcal polypeptide antigens. In other embodiments, the composition includes no additional staphylococcal antigens. In yet another embodiment, the composition includes no additional antigens.

The invention also provides a lyophilizate of the immunogenic composition of the invention. This lyophilizate can be reconstituted with aqueous material to provide an aqueous immunogenic composition of the invention. For administration, the lyophilizate is thus reconstituted with a suitable liquid diluent (e.g. a buffer, saline solution, water for injections (WFI)). The liquid diluent can include an adjuvant e.g. an aluminium salt or an oil-in-water emulsion adjuvant.

Sta006

The 'Sta006' antigen is disclosed as a useful immunogen in ReferenceReference 5. It was originally annotated as 'ferrichrome-binding protein', and has also been referred to as 'FhuD2' in the literature [7]. In the NCTC 8325 strain, Sta006 is SAOUHSC_02554 and has amino acid sequence SEQ ID NO: 1 (GI: 88196199). In the Newman strain it is nwmn_2185 (GI: 151222397). Mutant forms of Sta006 are reported in Reference 8. The known Sta006 antigen has a N-terminus cysteine in its mature form which may be lipidated. Wild-type cysteine-containing Sta006 can exist as a monomer or an oligomer (e.g. covalent dimer).

The invention uses a variant form of Sta006 that cannot form covalent dimers via disulphide bonds. The polypeptide does not contain any free thiol group (under reducing conditions). It can elicit antibodies (e.g. when administered to a human) which recognise a wild-type Sta006 antigen (e.g. SEQ ID NO: 2). The polypeptide may comprise an amino acid sequence having 80% or more identity (e.g. 85%, 90%, 91%, 92%, 93%, 94%, 95%, 96%, 97%, 98%, 99%, 99.5% or more) to any of SEQ ID NOs: 4, 5, 6 and 7. SEQ ID NO: 4 is amino acid residues 19-302 of SEQ ID NO: 1. Compared to SEQ ID NO: 4, SEQ ID NO: 5 has an additional amino acid residue 'X' at the N-terminus, wherein 'X' is an amino acid that does not contain a free thiol group. Compared to SEQ ID NO: 4, SEQ ID NO: 6 has a Met-Ala-Ser-sequence at the N-terminus. Compared to SEQ ID NO: 5, SEQ ID NO: 7 has a Met-Ala-Ser-sequence at the N-terminus A Sta006 polypeptide comprising any of SEQ ID NOs: 4, 5, 6 and 7 can be used with the invention.

A useful variant form of Sta006 may comprise at least one point mutation that replaces, modifies or deletes the cysteine residue present in the wild-type form of the antigen. For example, a Sta006 polypeptide may comprise an amino acid sequence having SEQ ID NO: 3, wherein the cysteine residue at position 4 of SEQ ID NO: 3 is replaced, modified or deleted. Preferably, the replacement is with a serine or an alanine residue. Alternatively, the cysteine residue is deleted (e.g. providing SEQ ID NO: 6).

Hybrid Polypeptides

Antigens used in the invention may be present in the composition as individual separate polypeptides. Where more than one antigen is used, however, they do not have to be present as separate polypeptides. Instead, at least two (e.g. 2, 3, 4, 5, or more) antigens can be expressed as a single polypeptide chain (a 'hybrid' polypeptide), as described in Reference 5. The hybrid polypeptide used with the invention ideally has no free thiol group (under reducing conditions).

Hybrids consisting of amino acid sequences from two, three, four, or more antigens are useful. In particular, hybrids consisting of amino acid sequences from two, three, four, or five antigens are preferred, such as two antigens.

Different hybrid polypeptides may be mixed together in a single formulation. The hybrid polypeptides can also be combined with conjugates or non-*S. aureus* antigens as described elsewhere herein.

Usefully, these hybrid polypeptides can elicit antibodies (e.g. when administered to a human) that recognise each of the wild-type staphylococcal proteins represented in the hybrid.

In some embodiments antigens in a single hybrid polypeptide are joined together by a linker amino acid sequence. Linker amino acid sequences will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, or poly-glycine linkers. Other suitable linker amino acid sequences will be apparent to those skilled in the art.

Polypeptides Used with the Invention

The invention uses variant forms of *S. aureus* antigens that do not form disulphide bonds. *S. aureus* antigens that contain free thiol groups (e.g. cysteine amino acids) can form oligomers, including covalent homo- or hetero-dimers in standard buffers. The covalent dimers are usually produced by oxidation of the thiol groups of cysteine residues resulting in a disulphide bond (i.e. the formation of a cystine). To eliminate covalent dimer formation, the polypeptides of the invention do not contain any free thiol groups (under reducing conditions) that can react to form disulphide bonds. A free thiol group, also known as an unprotected thiol group, or a free or unprotected —SH, has a reactive sulphur atom. A cysteine amino acid residue has a free thiol group (under reducing conditions), and thus the polypeptides of the invention do not contain any cysteine amino acid residue. A cysteine residue can be derivatised such that the thiol group is protected and cannot react to form disulphide bonds, e.g. by adding a thiol protecting group. Thiol protecting groups are known in the art, e.g. thioether, thioester or derivatives thereof [9]. Thus, the polypeptides of the invention may contain derivatised cysteine amino acid residues, provided that the derivatised cysteine amino acid residues do not have free thiol groups (under reducing conditions) that can form disulphide bonds.

In some exceptional embodiments, a polypeptide can include a thiol group, but this thiol group is not part of the side chain in a cysteine residue. Ideally, however, a polypeptide includes no thiol groups at all.

Preferably the polypeptide contains neither cysteine nor cystine.

In some embodiments, the polypeptide may contain amino acid 'X'. 'X' can be any amino acid, provided that it does not contain a free thiol group. The amino acid can be a natural or a non-natural amino acid. Natural amino acids are known in the art, e.g. alanine, arginine, asparagine, aspartic acid, glutamine, glutamic acid, glycine, histidine, isoleucine, leucine lysine, methionine, phenylalanine, proline, serine, threonine, tryptophan, tyrosine or valine. Cysteine has a free thiol group, and so 'X' cannot be a cysteine residue. A non-natural amino acid can be a derivatised or modified amino acid. 'X' can be a derivatised amino acid that does not contain a free thiol group, e.g. methyl-cysteine.

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides used with the invention can be prepared by various means (e.g. recombinant expression, purification from cell culture, chemical synthesis, etc.). Recombinantly-expressed proteins are preferred, particularly for hybrid polypeptides.

Antigens in composition of the invention are separated from the organism in which they were expressed. Sta006 polypeptides are thus provided in purified or substantially purified for before being used i.e. substantially free from other staphylococcal or host cell polypeptides. A Sta006 polypeptide is generally at least about 80% pure (by weight) before being used with the invention, and usually at least about 90% pure i.e. less than about 20%, and preferably less than about 10% (e.g. <5%) of a Sta006 composition is made up of other polypeptides.

Preferred polypeptides used with the invention have a N-terminus methionine, but in some embodiments a methionine which was present at the N-terminus of a nascent polypeptide may be absent from the polypeptide in a composition of the invention.

Polypeptides used with the invention are preferably staphylococcal polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulphide bond formation, glycosylation, lipidation, acetylation, phosphorylation, or any other manipulation or modification, such as conjugation with a labelling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence -P-Q- or -Q-P-, wherein: -P- is an amino acid sequence as defined above and -Q- is not a sequence as defined above i.e. the invention provides fusion proteins, provided that the polypeptides do not contain any free thiol group. Where the N-terminus codon of -P- is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more), maltose-binding protein, or glutathione-S-transferase (GST).

Although expression of the polypeptides of the invention may take place in a *Staphylococcus*, the invention will usually use a heterologous host for expression (recombinant expression). The heterologous host may be prokaryotic (e.g. a bacterium) or eukaryotic. It may be *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc. Compared to the wild-type *S. aureus* genes encoding polypeptides of the invention, it is helpful to change codons to optimise expression efficiency in such hosts without affecting the encoded amino acids.

Nucleic Acids

The invention provides nucleic acid encoding polypeptides and hybrid polypeptides of the invention. It also provides nucleic acid comprising a nucleotide sequence that encodes one or more polypeptides or hybrid polypeptides of the invention.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

Methods of manipulating nucleic acids and expressing the encoded proteins are known in the art, and include those described in References 43 and 67. A nucleic acid sequence may be modified by replacing the codon for cysteine with a codon for another amino acid. The cysteine may be replaced with any other amino acid, including serine, alanine, glycine, valine, leucine, or isoleucine, or modified forms of an amino acid that does not have free thiol groups (i.e. cannot readily form disulphide bonds). Alternatively, the cysteine residue may simply be deleted from the sequence. Thus, a deletion must remove the codon for the cysteine from the nucleic acid sequence without introducing a frameshift. Techniques for making substitution and deletion mutations at predetermined sites in a nucleic acid having a known sequence are well known and include, but are not limited to, primer mutagenesis and other forms of site-directed mutagenesis.

The invention also provides nucleic acid comprising nucleotide sequences having sequence identity to such nucleotide sequences. Identity between sequences is preferably determined by the Smith Waterman homology search algorithm as described above. Such nucleic acids include those using alternative codons to encode the same amino acid.

Nucleic acid according to the invention can take various forms (e.g. single stranded, double stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double stranded form. Nucleic acids of the invention are preferably provided in purified or substantially purified form i.e. substantially free from other nucleic acids (e.g. free from naturally-occurring nucleic acids), particularly from other staphylococcal or host cell nucleic acids, generally being at least about 50% pure (by weight), and usually at least about 90% pure. Nucleic acids of the invention are preferably staphylococcal nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA.

Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Strains and Variants

An exemplary amino acid and nucleotide sequence for the antigens described herein can easily be found in public sequence databases from the NCTC 8325 and/or Newman *S. aureus* strain using their GI numbers, for example, but the invention is not limited to sequences from the NCTC 8325 and Newman strains. Genome sequences of several other strains of *S. aureus* are available, including those of MRSA strains N315 and Mu50 [10], MW2, N315, COL, MRSA252, MSSA476, RF122, USA300 (very virulent), JH1 and JH9. Standard search and alignment techniques can be used to identify in any of these (or other) further genome sequences the homolog of any particular sequence from the Newman or NCTC 8325 strain. Moreover, the available sequences from the Newman and NCTC 8325 strains can be used to design primers for amplification of homologous sequences from other strains. Thus the invention is not limited to these two strains, but rather encompasses such variants and homologs from other strains of *S. aureus*, as well as non-natural variants. In general, suitable variants of a particular SEQ ID NO include its allelic variants, its polymorphic forms, its homologs, its orthologs, its paralogs, its mutants, etc., provided they do not contain any free thiol group.

Thus, for instance, polypeptides used with the invention may, compared to the SEQ ID NO herein, include one or more (e.g. 1, 2, 3, 4, 5, 6, 7, 8, 9, etc.) amino acid substitutions, such as conservative substitutions (i.e. substitutions of one amino acid with another which has a related side chain), provided that the new amino acid residue does not contain a free thiol group. The polypeptides of the invention do not contain any cysteine residue. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptide of the invention cannot be substituted with a cysteine. The polypeptides may also include one or more (e.g. 1, 2, 3, 4, 5, 6, 7, 8, 9, etc.) single amino acid deletions relative to the SEQ ID NO sequences. The polypeptides may also include one or more (e.g. 1, 2, 3, 4, 5, 6, 7, 8, 9, etc.) insertions (e.g. each of 1, 2, 3, 4 or 5 amino acids) relative to the SEQ ID NO sequences, provided that the inserted amino acid residue does not contain any free thiol group (e.g. the inserted amino acid is not a cysteine).

Similarly, a polypeptide used with the invention may comprise an amino acid sequence that:

is identical (i.e. 100% identical) to a sequence disclosed in the sequence listing;

shares sequence identity (e.g. 80%, 85%, 90%, 91%, 92%, 93%, 94%, 95%, 96%, 97%, 98%, 99%, 99.5% or more) with a sequence disclosed in the sequence listing;

has 1, 2, 3, 4, 5, 6, 7, 8, 9 or 10 (or more) single amino acid alterations (deletions, insertions, substitutions), which may be at separate locations or may be contiguous, as compared to the sequences of (a) or (b); and when aligned with a particular sequence from the sequence listing using a pairwise alignment algorithm, each moving window of x amino acids from N-terminus to C-terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [11], using default parameters (e.g. with Gap opening penalty=10.0, and with Gap extension penalty=0.5, using the EBLOSUM62 scoring matrix). This algorithm is conveniently implemented in the needle tool in the EMBOSS package [12];

provided that the polypeptide does not contain any free thiol group.

Where hybrid polypeptides are used, the individual antigens within the hybrid (i.e. individual -X-moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2 \neq X_3$ (iii) $X_1 \neq X_2=X_3$ (iv) $X_1 \neq X_2 \neq X_3$ or (v) $X_1=X_3 \neq X_2$, etc.

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus. N-terminus truncation can remove leader peptides e.g. to facilitate recombinant expression in a heterologous host. C-terminus truncation can remove anchor sequences e.g. to facilitate recombinant expression in a heterologous host.

In general, when an antigen comprises a sequence that is not identical to a complete *S. aureus* sequence from the sequence listing (e.g. when it comprises a sequence listing with <100% sequence identity thereto, or when it comprises a fragment thereof) it is preferred in each individual instance that the antigen can elicit an antibody which recognises the respective complete *S. aureus* sequence.

Combinations with Saccharides

The immunogenic compositions of the invention may further comprise saccharide antigens (e.g. known saccharide antigens include the exopolysaccharide of *S. aureus*, which is a poly-N-acetylglucosamine (PNAG), and the capsular saccharides of *S. aureus*, which can be e.g. from type 5, type 8 or type 336). In some embodiments a composition does not include a *S. aureus* saccharide antigen.

Combinations with Non-staphylococcal Antigens

The immunogenic compositions of the invention may further comprise non-staphylococcal antigens, and in particular with antigens from bacteria associated with nosocomial infections. For example, the immunogenic composition may further comprise one or more antigen(s) selected from the group consisting of: *Clostridium difficile*; *Pseudomonas aeruginosa*; *Candida albicans*; and extraintestinal pathogenic *Escherichia coli*. Further suitable antigens for use in combination with staphylococcal antigens of the invention are listed on pages 33-46 of Reference 13.

Preferred Compositions

In some embodiments the composition may include one or more further polypeptides. If the composition does include one or more further polypeptides, it is preferred that these do not contain any free thiol groups. Preferably, the further polypeptides are staphylococcal polypeptides, e.g. the *S. aureus* polypeptides disclosed in Reference 5.

The composition of the invention is particularly useful when using TLR7 agonists of formula (K). These agonists are discussed in detail in ReferenceReference 14:

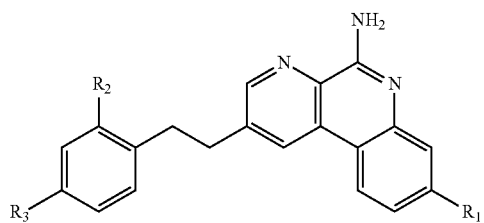

(K)

wherein:
$R^1$ is H, $C_1$-$C_6$alkyl, —$C(R^5)_2$OH, -$L^1R^5$, -$L^1R^6$, -$L^2R^5$, -$L^2R^6$, —$OL^2R^5$, or —$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH;
each $R^4$ is independently selected from H and fluoro;
$R^5$ is —$P(O)(OR^9)_2$,
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6; and
q is 1, 2, 3 or 4.

The compound of formula (K) is preferably of formula (K'):

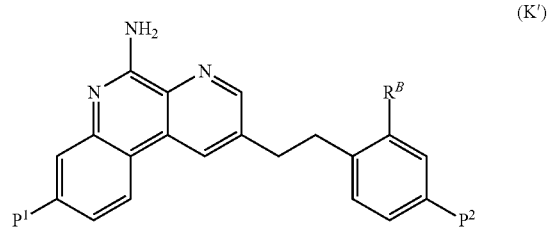

wherein:
$P^1$ is selected from H, $C_1$-$C_6$alkyl optionally substituted with COOH and —Y-L-X—P(O)(OR$^X$)(OR$^Y$);
$P^2$ is selected from H, $C_1$-$C_6$alkyl, $C_1$-$C_6$alkoxy and —Y-L-X—P(O)(OR$^X$)(OR$^Y$);
with the proviso that at least one of $P^1$ and $P^2$ is —Y-L-X—P(O)(OR$^X$)(OR$^Y$);
$R^B$ is selected from H and $C_1$-$C_6$alkyl;
$R^X$ and $R^Y$ are independently selected from H and $C_1$-$C_6$alkyl;
X is selected from a covalent bond, O and NH;
Y is selected from a covalent bond, O, C(O), S and NH;
L is selected from, a covalent bond $C_1$-$C_6$alkylene, $C_1$-$C_6$alkenylene, arylene, heteroarylene, $C_1$-$C_6$alkyleneoxy and —$((CH_2)_pO)_qCH_2)_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6; and
q is selected from 1, 2, 3 and 4.

In some embodiments of formula (K'): $P^1$ is selected from $C_1$-$C_6$alkyl optionally substituted with COOH and —Y-L-X—P(O)(OR$^X$)(OR$^Y$); $P^2$ is selected from $C_1$-$C_6$alkoxy and —Y-L-X—P(O)(OR$^X$)(OR$^Y$); $R^B$ is $C_1$-$C_6$alkyl; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

A preferred compound of formula (K) for use with the invention is 3-(5-amino-2-(2-methyl-4-(2-(2-(2-phosphonoethoxy) ethoxy)ethoxy)phenethyl)benzo[f] [1,7] naphthyridin-8-yl)propanoic acid, or compound 'K1':

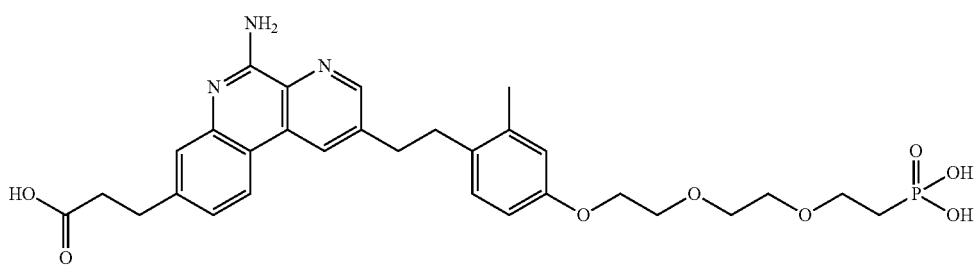

(K1)

This compound can be used as free base or in the form of a pharmaceutically acceptable salt e.g. an arginine salt.

Compounds of formula (K) can be mixed with an insoluble metal salt (preferably an aluminium salt, such as an aluminium hydroxide), and the compound is typically adsorbed to the metal salt. The Sta006 antigen (and, optionally, further antigen(s) in a composition) can also be adsorbed to the metal salt. Thus a preferred composition comprises (i) a Sta006 antigen as defined herein (ii) a TLR7 agonist of formula (K), such as formula (K1), and (iii) an insoluble metal salt, such as an aluminium hydroxide. The TLR7 agonist and the Sta006 antigen are preferably adsorbed to the metal salt.

Stabilizing Additives

In some embodiments of the invention an immunogenic composition includes a stabilizing additive. Such additives include, but are not limited to, chelators of divalent metal cations (e.g. EDTA, ethylenediaminetetraacetic acid), sugars (e.g. disaccharides such as sucrose or trehalose), sugar alcohols (e g. mannitol), free amino acids (e.g. arginine), buffer salts (e.g. phosphate, citrate), polyols (e.g. glycerol, mannitol), or protease inhibitors.

EDTA is a preferred additive. The final concentration of EDTA in the immunogenic composition of the invention can be about 1-50 mM, about 1-10 mM or about 1-5 mM, preferably about 2.5 mM.

A buffer is another useful additive, in order to control pH of a composition. This can be particularly important after reconstitution of lyophilized material. Compositions of the invention may include one or more buffer(s). Typical buffers include: a phosphate buffer; a Tris buffer; a borate buffer; a succinate buffer; a histidine buffer; or a citrate buffer. A phosphate buffer is preferable. Buffers will typically be included in the 5-20 mM range. Aqueous compositions of the invention preferably have a pH of between 5 and 8 e.g. between 5.5-6.5, or 5.9-6.1, or a pH of 6.

A saccharide or sugar alcohol (or mixture thereof e.g. a mannitol sucrose mixture) is also useful, particularly when using lyophilization. Suitable materials include, but are not limited to, mannitol, lactose, sucrose, trehalose, dextrose, etc. The use of sucrose is particularly preferred. Such materials can be present at a concentration of about 1% by weight per volume, or about 3% to about 6% by weight per volume, or up to about 10% or about 12.5% by weight per volume, preferably about 5% by weight per volume.

Lyophilization

One way of storing immunogenic compositions of the invention is in lyophilized form. This procedure can be used with or without the addition of a metal chelator (e.g. EDTA). The inventors have also shown that EDTA does not have a significant impact on the thermal characteristic of the vaccine and does not introduce any undesired plasticizing effect, thus meaning that EDTA-containing compositions can be lyophilized to further enhance storage stability.

Thus, generally, the invention also provides a lyophilizate which comprises a divalent metal cation chelator (e.g. EDTA) and at least one antigen (e.g. at least one polypeptide antigen).

The invention also provides a lyophilizate of an aqueous immunogenic composition of the invention. This is prepared by lyophilising an aqueous composition of the invention. It can then be reconstituted with aqueous material to provide an aqueous immunogenic composition of the invention. Materials present in the material which is lyophilized will remain in the lyophilizate and will thus also be present after reconstitution e.g. buffer salts, lyoprotectants (e.g. sucrose and/or mannitol), chelators, etc. If the material is reconstituted with a smaller volume of material than before lyophilization then these materials will be present in more concentrated form. The reconstituted lyophilizate preferably contains lyoprotectants (e.g. sucrose and/or mannitol) at a concentration of up to about 2.5% by weight per volume, preferably about 1% to about 2% by weight per volume. The amount of EDTA which is present in a composition prior to lyophilization is ideally at least 0.75 mM, and preferably at least 2.5 mM. A maximum of 50 mM is envisaged.

Liquid materials useful for reconstituting lyophilizates include, but are not limited to: salt solutions, such as physiological saline; buffers, such as PBS; water, such as wfi. They usefully have a pH between 4.5 and 7.5 e.g. between 6.8 and 7.2. The reconstituted lyophilizate preferably has a pH of between 5-6.5 e.g. between 5.8-6.2, or 5.9-6.1, or a pH of 6. A liquid material for reconstitution can include an adjuvant e.g. an aluminium salt adjuvant. Aqueous suspensions of adjuvants (optionally including buffers, such as a histidine buffer) are useful for simultaneously reconstituting and adsorbing lyophilized polypeptides. In other embodiments the liquid material is adjuvant-free. Typically the lyophilizate does not include an insoluble metal salt adjuvant.

The invention also provides a lyophilizate which comprises EDTA and at least one antigen.

Immunogenic Compositions and Medicaments

Immunogenic compositions of the invention may be useful as vaccines. Vaccines according to the invention may either be prophylactic (i.e. to prevent infection) or therapeutic (i.e. to treat infection), but will typically be prophylactic.

Compositions may thus be pharmaceutically acceptable. They will usually include components in addition to the antigens e.g. they typically include one or more pharmaceutical carrier(s) and/or excipient(s). A thorough discussion of such components is available in ReferenceReference 40.

Compositions will generally be administered to a mammal in aqueous form. Prior to administration, however, the composition may have been in a non-aqueous form. For instance, although some immunogenic compositions are manufactured in aqueous form, then filled and distributed and administered also in aqueous form, other immunogenic compositions are lyophilized during manufacture and are reconstituted into an aqueous form at the time of use. Thus a composition of the invention may be dried, such as a lyophilized formulation.

Where a composition of the invention includes more than one polypeptide, the mass of each different polypeptide can be the same or different. Ideally they are present at substantially equal masses i.e. the mass of each of them is within ±5% of the mean mass of all the polypeptides. In embodiments where two antigens are present as a hybrid polypeptide, the hybrid is considered as a single polypeptide for this purpose. The factors that can influence the amount of the polypeptide to be included in a multivalent formulation include the amount of polypeptide sufficient to elicit an immune response and the amount that would cause aggregation (with itself or with other polypeptide) or influence the stability of the other polypeptide. Typical masses of a polypeptide in an immunogenic composition are between 1-100μg.

The composition may include preservatives such as thiomersal or 2-phenoxyethanol. It is preferred, however, that the immunogenic compositions should be substantially free from (i.e. less than 5 μg/ml) mercurial material e.g. thiomersal-free. Compositions containing no mercury are more preferred. Preservative-free compositions are particularly preferred.

To improve thermal stability, a composition may include a temperature protective agent. Further details of such agents are provided below. To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminium hydroxide adjuvant); or a citrate buffer. Buffers will typically be included in the 5-20 mM range. The buffer is preferably 10 mM potassium phosphate.

The pH of the compositions are preferably between about 5 and about 8, and more preferably between about 5.5 and about 6.5, and most preferably at about 6.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below. Thus the immunogenic compositions may further comprise an adjuvant, such as an aluminium salt adjuvant (for example, one or more antigens may be adsorbed to aluminium salt). More generally, adjuvants which may be used in compositions of the invention include, but are not limited to, those already listed in ReferenceReference 5. These include mineral-containing adjuvants and oil-in-water emulsions.

Mineral-containing Adjuvants

Mineral containing adjuvants include mineral salts such as aluminium salts and calcium salts (or mixtures thereof). Preferably, the composition contains an aluminium salt adjuvant. Aluminium salts include hydroxides, phosphates, etc., with the salts taking any suitable form (e.g. gel, crystalline, amorphous, etc.). Calcium salts include calcium phosphate (e.g. the "CAP" particles disclosed in Ref 15). Adsorption to these salts is preferred (e.g. all antigens may be adsorbed). The mineral containing compositions may also be formulated as a particle of metal salt [16].

The adjuvants known as aluminium hydroxide and aluminium phosphate may be used. These names are conventional, but are used for convenience only, as neither is a precise description of the actual chemical compound which is present (e.g. see chapter 9 of ReferenceReference 17)). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulphate (i.e. aluminium hydroxyphosphate sulphate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4$/Al molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.1-10 μm (e.g. about 0.1-5 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The preferred aluminium salt adjuvant is an aluminium hydroxide adjuvant.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

A mineral salt can usefully have a TLR agonist, such as a TLR7 agonist, adsorbed to it (e.g. see Ref 18). The adsorbed TLR7 agonist is usefully a compound of formula (K) as described above.

Oil & Water Emulsions

Oil emulsion compositions suitable for use as adjuvants in the invention include oil-in-water emulsions such as MF59 (Chapter 10 of Ref 17; see also Ref 19) and AS03. Complete Freund's adjuvant (CFA) and incomplete Freund's adjuvant (IFA) may also be used.

Various oil-in-water emulsion adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of ≤1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, polysorbate 80, and sorbitan trioleate. These three components can be present at a volume ratio of 10:1:1 or a weight ratio of 39:47:47. The composition of the emulsion by volume can be about 5% squalene, about 0.5% polysorbate 80 and about 0.5% sorbitan trioleate. In weight terms, these ratios become 4.3% squalene, 0.5% polysorbate 80 and 0.48% sorbitan trioleate. This adjuvant is known as 'MF59' [20-22], as described in more detail in Chapter 10 of Ref 23 and chapter 12 of Ref 24. The MF59 emulsion advantageously includes citrate ions e.g. 10 mM sodium citrate buffer.

An emulsion of squalene, a tocopherol, and polysorbate 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% polysorbate 80, and the weight ratio of squalene:tocopherol is preferably ≤1 as this provides a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [25] e.g. in the ratios discussed above.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 m/ml polysorbate 80, 110 m/ml Triton X-100 and 100 m/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [26] (0.05-1% Thr-MDP, 5% squalane, 2.5% Pluronic L121 and 0.2% polysorbate 80). It can also be used without the Thr-MDP, as in the "AF" adjuvant [27] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [28]. The emulsion may also include one or more of: alditol; a cryoprotective agent (e.g. a sugar, such as dodecylmaltoside and/or sucrose); and/or an alkylpolyglycoside. The emulsion may include a TLR4 agonist [29]. Such emulsions may be lyophilized.

An emulsion of squalene, poloxamer 105 and Abil-Care [30]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in ReferenceReference 31, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in Reference 32, produced by addition of aliphatic amine to desacylsaponin via the carboxyl group of glucuronic acid), dimethyidioctadecylammonium bromide and/or N,N-dioctadecyl-N, N-bis(2-hydroxyethyl)propanediamine An emulsion in which a saponin (e.g. QuilA or QS21) and a sterol (e.g. a cholesterol) are associated as helical micelles [33].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [34].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [34].

In some embodiments an emulsion may be mixed with antigen extemporaneously, at the time of delivery, and thus the adjuvant and antigen may be kept separately in a packaged or distributed composition, ready for final formulation at the time of use. In other embodiments an emulsion is mixed with antigen during manufacture, and thus the composition is packaged in a liquid adjuvanted form. The antigen will generally be in an aqueous form, such that the composition is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in compositions for use in elderly patients (e.g. aged 60 years or older) because vitamin E has been reported to have a positive effect on the immune response in this patient group [35]. They also have antioxidant properties that may help to stabilize the emulsions [36]. A preferred α-tocopherol is DL-α-tocopherol, and the preferred salt of this tocopherol is the succinate.

The use of an aluminium hydroxide and/or aluminium phosphate adjuvant is particularly preferred, and antigens are generally adsorbed to these salts.

Compositions of the invention may elicit both a cell mediated immune response as well as a humoral immune response. This immune response will preferably induce long lasting (e.g. neutralising) antibodies and a cell mediated immunity that can quickly respond upon exposure to *S. aureus*.

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

*S. aureus* infections can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilized composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilized antigens.

Where a composition is to be prepared extemporaneously prior to use (e.g. where a component is presented in lyophilized form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in Reference 37, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

Methods of Treatment, and Administration of the Vaccine

The invention also provides a method for raising an immune response in a mammal comprising the step of administering a composition of the invention to the mammal. The immune response is preferably protective and preferably involves antibodies and/or cell-mediated immunity. The method may raise a booster response.

At least some of the antibodies raised in response to polypeptides which are administered in accordance with the invention should be protective.

The invention also provides the use of a variant form of a Sta006 antigen, provided that the variant does not contain any free thiol group, in the manufacture of a medicament for raising an immune response in a mammal. It may also involve the use of an adjuvant.

By raising an immune response in the mammal by these uses and methods, the mammal can be protected against *S. aureus* infection, including a nosocomial infection. More particularly, the mammal may be protected against a skin infection, pneumonia, meningitis, osteomyelitis endocarditis, toxic shock syndrome, and/or septicaemia.

The invention also provides a kit comprising a first component and a second component wherein neither the first component nor the second component is a composition of the invention as described above, but wherein the first component and the second component can be combined to provide a composition of the invention as described above. The kit may further include a third component comprising one or more of the following: instructions, syringe or other delivery device, adjuvant, or pharmaceutically acceptable formulating solution.

The invention also provides a delivery device pre-filled with an immunogenic composition of the invention.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Other mammals which can usefully be immunised according to the invention are cows, dogs, horses, and pigs.

One way of checking efficacy of therapeutic treatment involves monitoring *S. aureus* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of immunogenic compositions can also be determined in vivo by challenging animal models of *S. aureus* infection, e.g., guinea pigs or mice, with the immunogenic compositions. In particular, there are three useful animal models for the study of *S. aureus* infectious disease, namely: (i) the murine abscess model [38], (ii) the murine lethal infection model [38] and (iii) the murine pneumonia model [39]. The abscess model looks at abscesses in mouse kidneys after intravenous challenge. The lethal infection model looks at the number of mice which survive after being infected by a normally-lethal dose of *S. aureus* by the intravenous or intraperitoneal route. The pneumonia model also looks at the survival rate, but uses intranasal infection. A useful immunogenic composition may be effective in one or more of these models. For instance, for some clinical situations it may be desirable to protect against pneumonia, without needing to prevent hematic spread or to promote opsonisation; in other situations the main desire may be to prevent hematic spread. Different antigens, and different antigen combinations, may contribute to different aspects of an effective immunogenic composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines prepared according to the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as an influenza vaccine, a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc. Further non-staphylococcal vaccines suitable for co-administration may include one or more antigens listed on pages 33-46 of Reference 13.

General

The practice of the present invention will employ, unless otherwise indicated, conventional methods of chemistry, biochemistry, molecular biology, immunology and pharmacology, within the skill of the art. Such techniques are explained fully in the literature. See, e.g., References 40-47, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN [48,49] or similar methods), or they can be predicted (e.g. using the Jameson-Wolf antigenic index [50], matrix-based approaches [51], MAPITOPE [52], TEPITOPE [53,54], neural networks [55], OptiMer & EpiMer [56, 57], ADEPT [58], Tsites [59], hydrophilicity [60], antigenic index [61] or the methods disclosed in References 62-66, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of Ref 67. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Ref 68. The percentage sequence identity between two sequences of different lengths is preferably calculated over the length of the longer sequence.

Phosphorous-containing adjuvants used with the invention may exist in a number of protonated and deprotonated forms depending on the pH of the surrounding environment, for example the pH of the solvent in which they are dissolved. Therefore, although a particular form may be illustrated, it is intended that these illustrations are merely representative and not limiting to a specific protonated or deprotonated form. For example, in the case of a phosphate group, this has been illustrated as $-OP(O)(OH)_2$ but the definition includes the protonated forms $[OP(O)(OH_2)(OH)]^+$ and $-[OP(O)(OH)_2]^{2+}$ that may exist in acidic conditions and the deprotonated forms $-[OP(O)(OH)(O)]-$ and $[OP(O)(O)_2]^{2-}$ that may exist in basic conditions.

Compounds can exist as pharmaceutically acceptable salts. Thus, compounds (e.g. adjuvants) may be used in the form of their pharmaceutically acceptable salts i.e. physiologically or toxicologically tolerable salt (which includes, when appropriate, pharmaceutically acceptable base addition salts and pharmaceutically acceptable acid addition salts).

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

Thermal Denaturation Assay

The Sta006 Cys(+) antigen used in the experiments described below is represented by SEQ ID NO: 3, and the Sta006 Cys(−) antigen is represented by SEQ ID NO: 6. Both antigens were recombinant proteins purified from *E. coli*.

Thermal stability of the Sta006 cysteine-containing Cys(+) antigen was compared to the Sta006 cystine-deficient Cys(−) antigen by Differential Scanning Fluorimetry (DSF). Samples containing antigen (10 µM in PBS) were heated under controlled conditions with a ramp rate of 1° C./min in Strategen Mx3000p Real Time PCR instrument. The dye SyproOrange 5× was used, and the changes in fluorescence were monitored. Assays were performed over a temperature range of 10-100° C.

Figure 1:
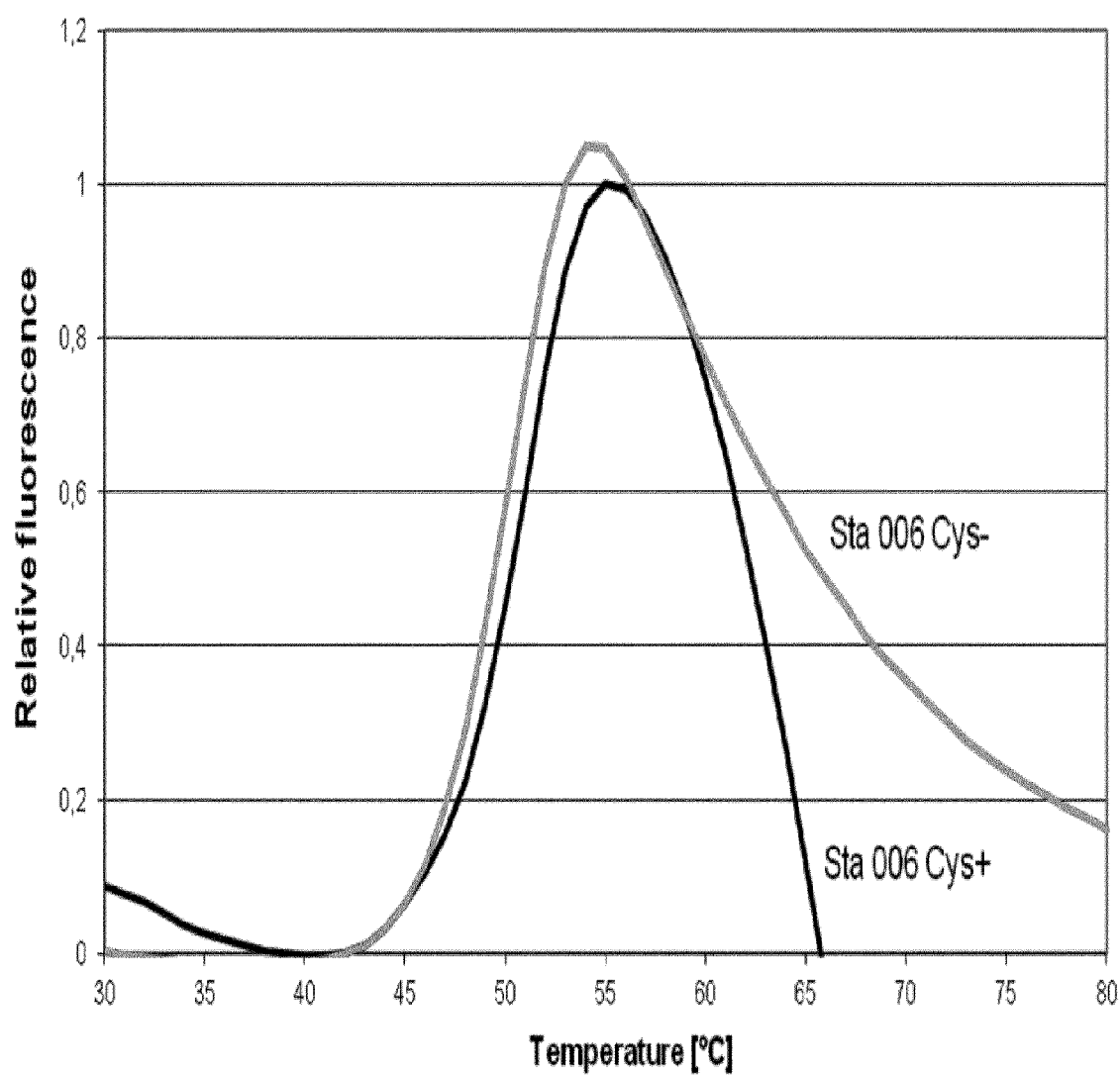
FIG. 1 shows the normalised melting curves of the cysteine-containing and cysteine-deficient Sta006 antigens.

FIG. 1 reports the melting curves of the antigens tested. It is shown that the peak for the Cys(−) antigen is shifted slightly to the top and left compared to the Cys(+) antigen. Melting temperatures (Tm) were determined by fitting the first derivative of the experimental curve. The Tm of Sta006 Cys(+) antigen was 50.16° C., and the Tm of Sta006 Cys(−) antigen was 49.62° C.

Thus, the thermal stability profile of the Sta006 Cys(−) antigen is comparable to the Sta006 Cys(+) antigen. Modifying the antigen by deleting or replacing the cysteine residue does not have a significant impact on the thermal stability of the Sta006 antigen.

Purification Process

The purification steps for the Sta006 Cys(+) antigen are explained below.
1. Lysis and clarification—cell lysis and clarification; adding a flocculating agent (PEI) that reduces DNA, endotoxins and proteic impurities.
2. SPFF chromatography—removal of HCP and other impurities.
3. Oxidative dimerization reaction—oxidation step.
4. cHT chromatography—removal of HCP and other residual impurities and separation of monomer from dimer
5. Final 10 kDa diafiltration—diafiltration in final buffer.

For purifying Sta006 Cys(−), the oxidative dimerization reaction step was no longer necessary as the antigen can be purified as a monomer. The cHT chromatography step was also simplified because it was no longer necessary to separate the monomer from the dimer.

Purity and yield of the Sta006 Cys (−) and Cys(+) antigens obtained from the process explained above was determined, and the results are shown in Table 1. Purity is determined using detector PDA 214 nm. Yield is calculated by: total proteins (mBCA content (mg/ml))×purity (RPC (%) 214 nm).

TABLE 1

Purity and yield of the Cys(−) and Cys(+) antigens.

| Antigen | Cys? | RP purity (%) | Yield (g/L ferm) |
|---|---|---|---|
| Sta006 | Cys(−) | 90.1 | 0.091<br>Biomass of fermentation recovered was about 54% (theoretical yield without slurry from centrifugation loss was: 1.176 g/L ferm) |
|  | Cys(+) | 95.8 | 0.012 |

The purified Sta006 Cys(−) antigen had comparable purity and yield to the Sta006 Cys(+) antigen. The analytical panel conformed to in-house specification limits. Removal of cysteine allowed higher flexibility in the purification process of the Sta006 antigen. The purification process can be further optimised in order to improve purity and yield.

Stability Evaluation

The stability of Sta006 Cys(−) antigen in a vaccine combination based on the disclosure of Reference 5 was investigated. The antigen was present at a concentration of 72 µg/mL. The vaccine combination was exposed to temperatures: 2-8° C., 15° C., 25° C. and 37° C. for 0 to 4 weeks. The highest temperature tested (37° C.) was below the Tm of the Sta006 Cys(−) antigen (about 50° C.). Hence, protein instability driven by the protein unfolding was not an influencing factor in this experiment.

Figure 2:
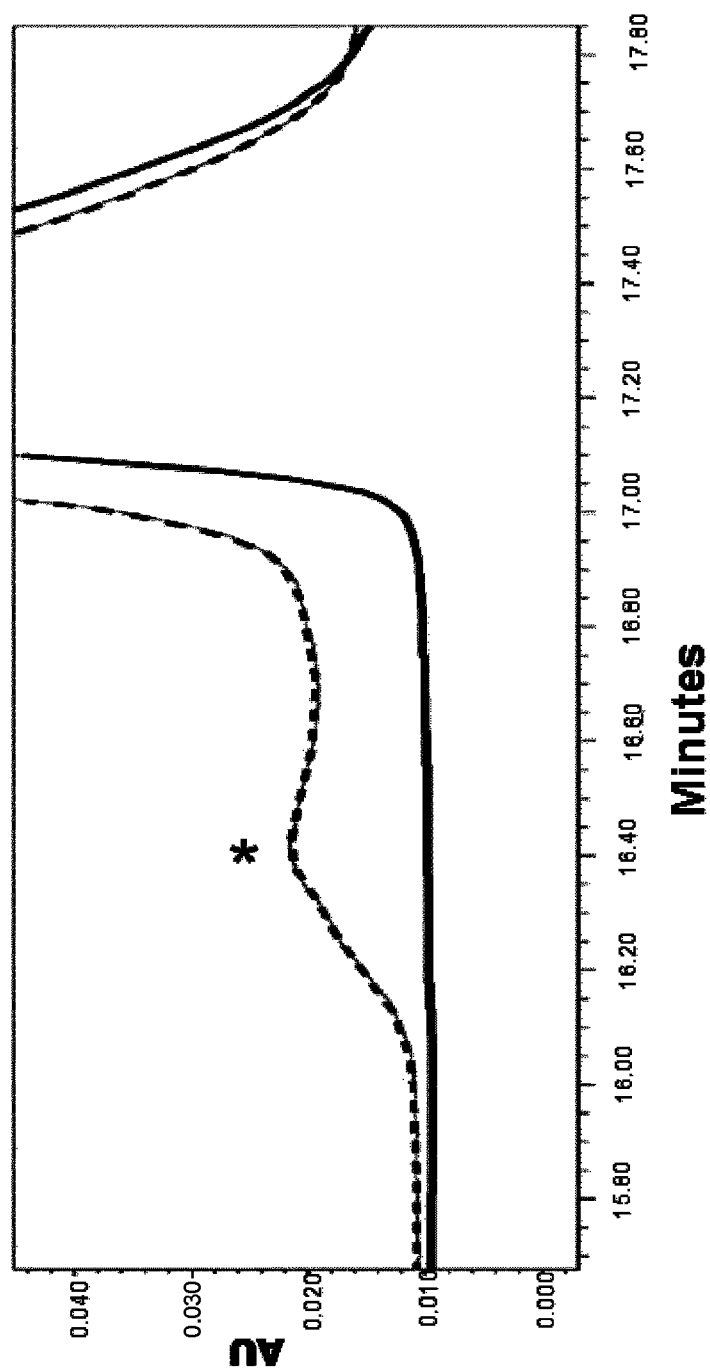
FIG. 2 shows the size exclusion chromatography (RP-HPLC) profile of Sta006 Cys(−) antigen after 4 weeks storage at 37° C. The RP-HPLC profile of Sta006 Cys(−) antigen without having undergone storage condition is shown as a control. * indicates additional peak of Sta006 Cys(−) antigen stored after 4 weeks at 37° C.

The samples were analysed using RP-HPLC, and the pH and osmolality were also analysed (3 determinations on 3 different vials at each temperature and timepoint). The osmolality and pH remained constant over time and within acceptable range. The Sta006 Cys(−) antigen was stable when stored for 4 weeks at 2-8° C., 15° C. and 25° C. However, when stored for 4 weeks at 37° C., there was 20-30% loss of antigen. FIG. 2 shows that the SEC profile of Sta006 Cys(−) antigen stored after 4 weeks at 37° C. has a small additional peak (*), suggesting the presence of degradation products. The area of the additional peak over total area is 2.9%. Hence, the Sta006 Cys(−) antigen was stable for up to 4 weeks at 2-8° C., 15° C. and 25° C.

The stability of Sta006 Cys(−) with aluminium hydroxide adjuvant was also assessed. It was observed that the Sta006 Cys(−) antigen was completely adsorbed onto Alum with adsorption >96%. No additional peaks revealed in the desorbed samples at any condition tested. For desorption, the samples were treated with 300 mM $KH_2PO_4$ pH 6.8 overnight at 25° C. The same conditions were applied for sample treatment at all time points (assumption: no influence of formulation aging).

Immunogenicity Studies in Mice

Immunogenicity of the Sta006 Cys(+) antigen was compared with the Sta006 Cys(−) antigen. The antigens were used in a combination based on the disclosure of Reference 5.

Five week old CD1 mice were immunized intraperitoneally with a prime-booster injection with the vaccines in 14-day interval Animals were bled immediately prior to the first immunization and 23 days thereafter, and sera were examined for IgG antibodies directed against the purified proteins using the Luminex technology. The assay read-out is a measure of fluorescence intensity expressed as arbitrary Relative Luminex Units (RLU/mL).

Figure 3:
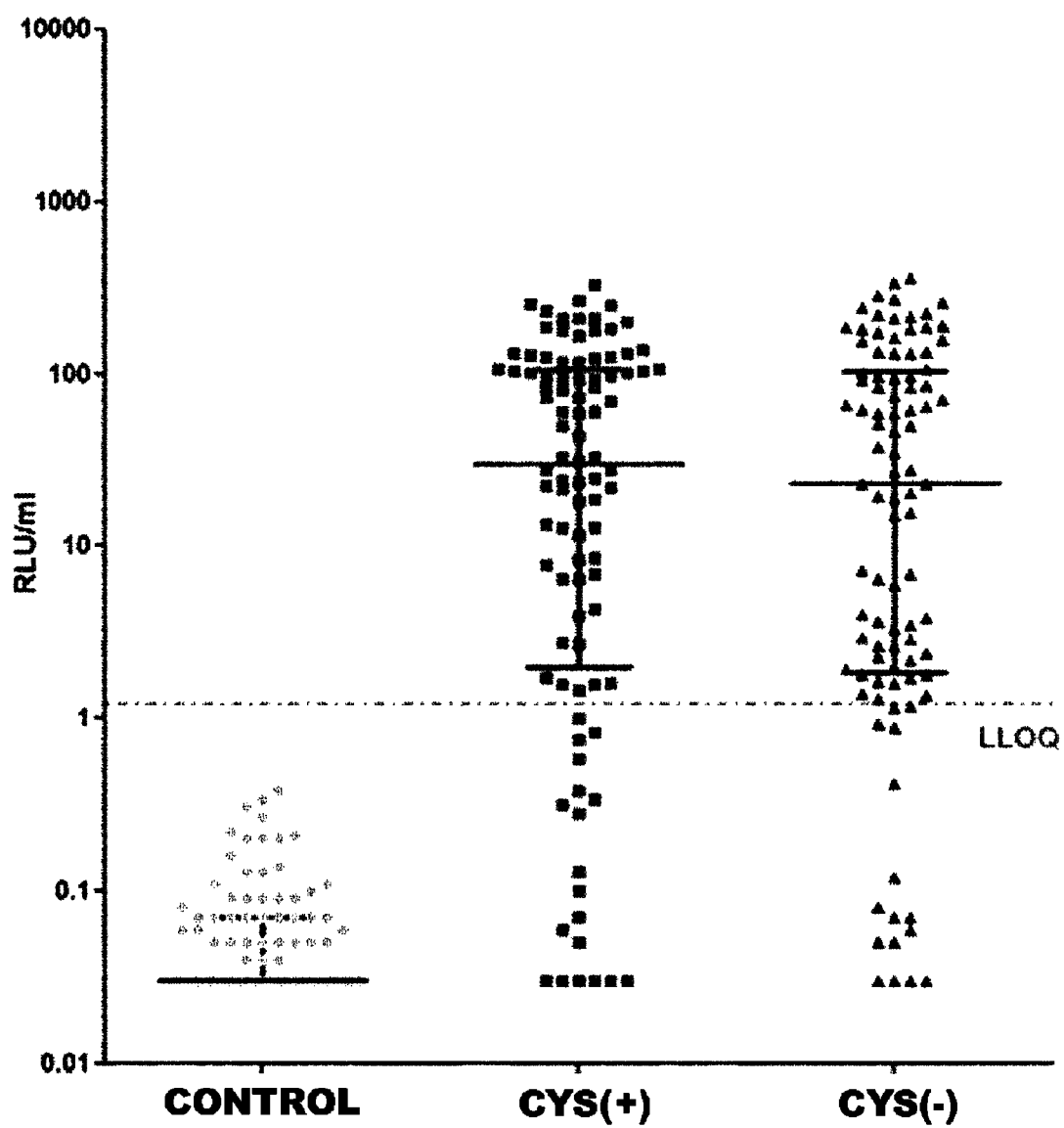
FIG. 3 shows anti-Sta006 antibody titres in CD1 mice which have been immunized with vaccine containing Sta006 Cys(+) antigen or Sta006 Cys(−) antigen Immunogenicity data for the control group is also shown.

FIG. 3 reports antibody titres of mice following immunization. The antibody titres for Sta006 antigen do not differ significantly between the Sta006 cysteine-containing Cys(+) antigen and the Sta006 cysteine-deficient Cys(−) variant.

In a further study, monovalent vaccines containing Sta006 Cys(−) and Sta006 Cys(+) antigens were compared. The vaccines were adjuvanted with aluminium hydroxide. Each vaccine contains 30 μg of antigen and aluminium hydroxide at 2 mg/ml.

Sixteen CD1 mice (five week old) were immunized subcutaneously three times (at t=0, 14 and 28 days). Animals were bled immediately prior to the first immunization, and 13, 27 and 42 days following the first immunization. The sera were examined for IgG antibodies directed against the purified proteins using the Luminex technology. The assay read-out is a measure of fluorescence intensity expressed as arbitrary Relative Luminex Units (RLU/mL).

It was found that antibodies were specifically elicited by monovalent vaccines containing the corresponding Cys(−) and Cys(+) antigens. There are no significant differences between the monovalent Sta006 Cys(−) and the Sta006 Cys(+) vaccines.

It will be understood that the invention is described above by way of example only and modifications may be made whilst remaining within the scope and spirit of the invention.

REFERENCES

[1] Harro et al. (2010) *Clin Vaccine Immunol* 17:1868-74.
[2] Kuklin et al. (2006) *Infect Immun.* 74(4):2215-23.
[3] Sheridan (2009) *Nature Biotechnology* 27:499-501.
[4] Merck and Intercell AG Announce Termination of Phase II/III Clinical Trial of Investigational *Staphylococcus aureus* Vaccine, V710—Merck Research and Development News—8 Jun. 2011
[5] WO2010/119343.
[6] U.S. provisional application 61/580,191.
[7] Sebulsky & Heinrichs (2001) *J Bacteriol* 183:4994-5000.
[8] Sebulsky et al. (2003) *J Biol Chem* 278:49890-900.
[9] Protective Groups in organic synthesis, Third Edition, Theodora W Greene, Peter G M Wuts, (1999) John Wiley, Chapter 6 Protection for the Thiol Group.
[10] Kuroda et al. (2001) *Lancet* 357:1225-1240.
[11] Needleman & Wunsch (1970) *J. Mol. Biol.* 48, 443-453.
[12] Rice et al. (2000) *Trends Genet* 16:276-277.
[13] WO2008/019162.
[14] WO2011/027222.
[15] U.S. Pat. No. 6,355,271.
[16] WO00/23105.
[17] Vaccine Design (1995) eds. Powell & Newman. ISBN: 030644867X. Plenum.
[18] WO2011/027222.
[19] WO90/14837.
[20] WO90/14837.
[21] Podda & Del Giudice (2003) *Expert Rev Vaccines* 2:197-203.
[22] Podda (2001) *Vaccine* 19: 2673-2680.
[23] Vaccine Design: The Subunit and Adjuvant Approach (eds. Powell & Newman) Plenum Press 1995 (ISBN 0-306-44867-X).
[24] Vaccine Adjuvants: Preparation Methods and Research Protocols (Volume 42 of *Methods in Molecular Medicine* series). ISBN: 1-59259-083-7. Ed. O'Hagan.
[25] WO2008/043774.
[26] Allison & Byars (1992) *Res Immunol* 143:519-25.
[27] Hariharan et al. (1995) *Cancer Res* 55:3486-9.
[28] US-2007/014805.
[29] US-2007/0191314.
[30] Suli et al. (2004) *Vaccine* 22(25-26):3464-9.
[31] WO95/11700.
[32] U.S. Pat. No. 6,080,725.
[33] WO2005/097181.
[34] WO2006/113373.
[35] Han et al. (2005) *Impact of Vitamin E on Immune Function and Infectious Diseases in the Aged at Nutrition, Immune functions and Health* EuroConference, Paris, 9-10 Jun. 2005.
[36] US-6630161.
[37] WO2006/110603.
[38] Stranger-Jones et al. (2006) *PNAS USA* 103:16942-7.
[39] Wardenburg et al. (2007) *Infect Immun* 75:1040-4.
[40] Gennaro (2000) *Remington: The Science and Practice of Pharmacy.* 20th edition, ISBN: 0683306472.
[41] Methods In Enzymology (S. Colowick and N. Kaplan, eds., Academic Press, Inc.)
[42] Handbook of Experimental Immunology, Vols. I-IV (D. M. Weir and C. C. Blackwell, eds, 1986, Blackwell Scientific Publications)
[43] Sambrook et al. (2001) *Molecular Cloning: A Laboratory Manual,* 3rd edition (Cold Spring Harbor Laboratory Press).
[44] Handbook of Surface and Colloidal Chemistry (Birdi, K. S. ed., CRC Press, 1997)
[45] Ausubel et al. (eds) (2002) *Short protocols in molecular biology,* 5th edition (Current Protocols).
[46] Molecular Biology Techniques: An Intensive Laboratory Course, (Ream et al., eds., 1998, Academic Press)
[47] PCR (Introduction to Biotechniques Series), 2nd ed. (Newton & Graham eds., 1997, Springer Verlag)
[48] Geysen et al. (1984) *PNAS USA* 81:3998-4002.
[49] Carter (1994) *Methods Mol Biol* 36:207-23.
[50] Jameson, B A et al. 1988, *CABIOS* 4(1):181-186.
[51] Raddrizzani & Hammer (2000) *Brief Bioinform* 1(2):179-89.
[52] Bublil et al. (2007) *Proteins* 68(1):294-304.
[53] De Lalla et al. (1999) *J. Immunol.* 163:1725-29.
[54] Kwok et al. (2001) *Trends Immunol* 22:583-88.
[55] Brusic et al. (1998) *Bioinformatics* 14(2):121-30
[56] Meister et al. (1995) *Vaccine* 13(6):581-91.
[57] Roberts et al. (1996) *AIDS Res Hum Retroviruses* 12(7):593-610.
[58] Maksyutov & Zagrebelnaya (1993) *Comput Appl Biosci* 9(3):291-7.
[59] Feller & de la Cruz (1991) *Nature* 349(6311):720-1.
[60] Hopp (1993) *Peptide Research* 6:183-190.
[61] Welling et al. (1985) *FEBS Lett.* 188:215-218.
[62] Davenport et al. (1995) *Immunogenetics* 42:392-297.
[63] Tsurui & Takahashi (2007) *J Pharmacol Sci.* 105(4):299-316.
[64] Tong et al. (2007) *Brief Bioinform.* 8(2):96-108.
[65] Schirle et al. (2001) *J Immunol Methods.* 257(1-2):1-16.
[66] Chen et al. (2007) *Amino Acids* 33(3):423-8.
[67] Current Protocols in Molecular Biology (F. M. Ausubel et al., eds., 1987) Supplement 30
[68] Smith & Waterman (1981) *Adv. Appl. Math.* 2: 482-489.

The invention claimed is:

1. An immunogenic composition comprising a stabilizing additive and a polypeptide comprising an amino acid sequence having at least 90% identity to the amino acid sequence of SEQ ID NO: 4, wherein the polypeptide does not contain the first eighteen amino acids of SEQ ID NO: 1, and wherein the polypeptide has no cysteine residues.

2. The composition of claim 1, wherein the polypeptide comprises the amino acid sequence of SEQ ID NO: 4, SEQ ID NO: 5, SEQ ID NO: 6, or SEQ ID NO: 7.

3. The immunogenic composition of claim 1, wherein the stabilizing additive is selected from the group consisting of chelators of divalent metal cations, sugars, sugar alcohols, free amino acids, buffer salts, polyols, and protease inhibitors.

4. The composition of claim 1, wherein the polypeptide is a hybrid protein.

5. The immunogenic composition of claim 1, further comprising one or more conjugates of (i) an *S.aureus* exopolysaccharide and (ii) a carrier protein.

6. The immunogenic composition of claim 1, further comprising one or more conjugates of (i) an *S.aureus* capsular polysaccharide and (ii) a carrier protein.

7. The immunogenic composition of claim 1, further comprising an adjuvant, or a combination of adjuvants.

8. The immunogenic composition of claim 1, in a lyophilized form.

9. The immunogenic composition of claim 1, in an aqueous form.

10. A vaccine comprising the immunogenic composition of claim 1.

11. A method for preparing an aqueous immunogenic composition, the method comprising the step of:
   reconstituting the immunogenic composition of claim 8 with aqueous material, so as to form the aqueous form.

* * * * *